United States Patent

Hamanaka et al.

[11] 4,332,644
[45] Jun. 1, 1982

[54] PROCESS FOR SEPARATING TRIOXANE

[75] Inventors: Katsuhiko Hamanaka; Toshiyuki Iwaisako; Junzo Masamoto; Koichi Yoshida, all of Fuji, Japan

[73] Assignee: Asahi Kasei Kogyo Kabushiki Kaisha, Osaka, Japan

[21] Appl. No.: 271,250

[22] Filed: Jun. 8, 1981

[51] Int. Cl.$^3$ .......................... B01D 3/34; B01D 11/04
[52] U.S. Cl. ......................................... 203/46; 203/69; 549/368
[58] Field of Search ..................... 260/340; 203/46, 69, 203/43-45

[56] References Cited

U.S. PATENT DOCUMENTS

| | | | |
|---|---|---|---|
| 3,201,419 | 8/1965 | Sennewald et al. | 260/340 |
| 3,313,713 | 4/1967 | Martin | 260/340 |
| 3,395,157 | 7/1968 | Dankert et al. | 260/340 |

Primary Examiner—Frank Sever
Attorney, Agent, or Firm—Wyatt, Gerber, Shoup, Scobey & Badie

[57] ABSTRACT

In a process for separating trioxane by a continuous distillation which comprises extracting, with benzene, the trioxane-containing distillate obtainable by heating an aqueous solution of formaldehyde, feeding the trioxane-containing benzene solution into a distillation column as a starting material, distilling out the benzene from the column top and withdrawing the trioxane from the column bottom, a process for separating trioxane which comprises retaining the concentration of trioxane X in the liquid composition at the starting material feeding plate of the distillation column (% by weight of trioxane based on the total liquid composition at the feeding plate) in the range satisfying the following relationship:

$$100 - \frac{50}{(\gamma - 0.5)} - 2(\gamma - 1)^{0.2} \leq X \quad (1)$$

$$\leq 100 - \frac{50}{(\gamma - 0.5)} - 2(\gamma - 1)^{0.2} + 2R^{0.5}$$

wherein R is reflux ratio, and $\gamma$ is a parameter defined by the following equation:

$$\gamma = \frac{R(1 - C/100) + q}{R(1 - C/100) - C/100 + q} \quad (2)$$

wherein q is the proportion of liquid part in the fed starting material as expressed in terms of ratio by weight and C (%) is the concentration of trioxane in the fed starting material.

4 Claims, 1 Drawing Figure

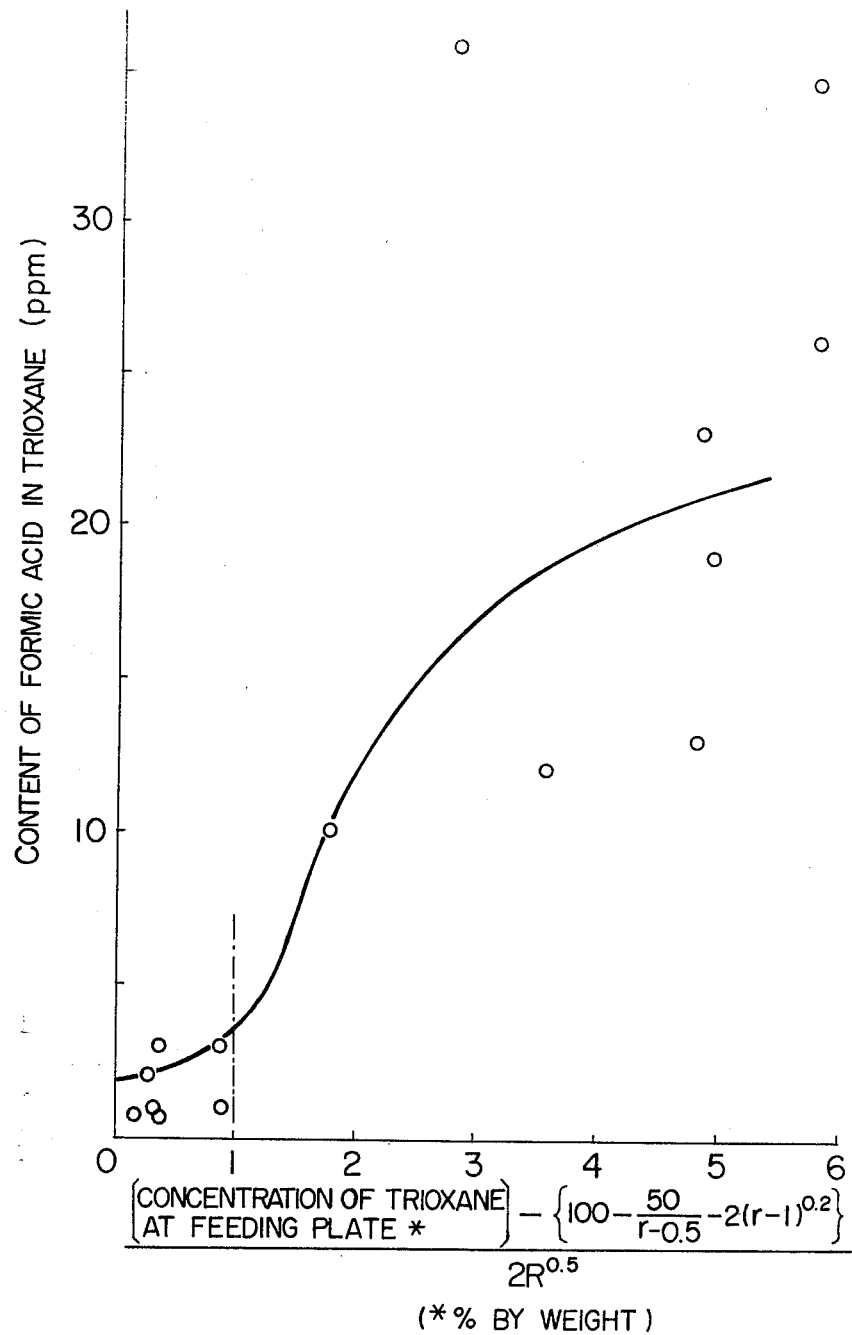

PROCESS FOR SEPARATING TRIOXANE

This invention relates to a process for separating trioxane obtainable by heating aqueous solution of formaldehyde, and more particularly to a process for separating trioxane which comprises extracting a trioxane-containing distillate obtainable by heating an aqueous solution of formaldehyde with benzene and then separating trioxane from this trioxane-containing benzene solution by a continuous distillation.

Trioxane is generally obtained by heating an aqueous solution of formaldehyde. As an industrial process for its production, there is proposed a process in which a distillate having a composition of 20–55% by weight trioxane, 10–35% by weight formaldehyde and 20–50% by weight water obtainable by heating and distilling an aqueous solution of formaldehyde having a concentration of 30–70% by weight in the presence of an acidic catalyst is used as the crude starting material.

The water present in the crude starting material and the formic acid present in the starting material which has been formed as a by-product owing to use of the strongly acidic catalyst in the trioxane-forming reaction act as chain transfer agent in the polymerization of trioxane into polyoxymethylene, so that they decrease the velocity of polymerization and makes the polymer production difficult. Further, the polymer thus obtained has a low degree of polymerization and therefore cannot have good physical properties. For this reason, they must be removed from the trioxane as exhaustively as possible.

As the process for removing water, there have been proposed a process which comprises adding an additive such as isocyanate, sodium dispersion, or metal hydride (French Pat. No. 1,359,595; West German Pat. No. 1,906,846; West German Pat. No. 1,280,884), a process which comprises adding an adsorbent such as alumina and zeolite (Japanese Patent Publication No. 17,915/69), a process which comprises distilling water in the presence of a solvent capable of making an azeotropic mixture with water (U.S. Pat. No. 3,522,278; Japanese Patent Publication No. 28,197/74; Japanese Patent Publication No. 28,518/74; U.S. Pat. No. 3,197,437), and so on.

However, these processes cannot always be said to be satisfactory as a process to be practised industrially for the reasons that some of them necessitate an after treatment because of the side reaction accompanied, that some of them are complicated in process, that some of them are insufficient in efficiency, and so on.

On the other hand, as the process for removing the formic acid in trioxane, there have been proposed a process which comprises adding an agent for capturing the formic acid such as alkali metals, isocyanates, metal hydroxides, or amines to the trioxane and rectifying it (U.S. Pat. No. 3,149,127; French Pat. No. 1,359,595; Belgian Pat. No. 647,355; Japanese Patent Publication No. 33,407/70) and a process which comprises adsorbing and removing the formic acid by using alumina, zeolite, ion exchange resin or the like as an adsorbent (Japanese Patent Publication No. 17,915/69; British Pat. No. 1,254,344; U.S. Pat. No. 3,395,157). There has also been proposed a process which comprises heating a concentrated aqueous solution of formaldehyde in the presence of a strongly acidic catalyst to form trioxane, extracting the aqueous distillate with benzene, fractionally distilling the benzene solution of trioxane to obtain a crude trioxane and then purifying the latter by distillation (U.S. Pat. No. 3,522,278). However, these processes cannot be said to be desirable as an industrial process in point that they necessitate a special chemical or a special equipment.

The present inventors conducted earnest studies with the aim of developing an industrial process by which a trioxane having low contents of water and formic acid could be obtained by a simple procedure with a high efficiency. As the result, it was found that a trioxane of high quality can be obtained by extracting, with benzene, a solution comprising trioxane, water and formaldehyde obtainable by heating and distilling an aqueous solution of formaldehyde and then distilling the benzene extract solution thus obtained under selected conditions. Based on this finding, this invention was accomplished.

Thus, this invention provides, in a process for separating trioxane by continuous distillation comprising extracting, with benzene, the trioxane-containing distillate obtainable by heating and distilling an aqueous solution of formaldehyde, feeding the benzene solution containing trioxane into a distillation column as a starting material, distilling out the benzene from the column top and withdrawing the trioxane from the column bottom, a process for separating trioxane characterized by retaining the concentration of trioxane, X in the liquid composition at the starting material feeding plate of the distillation column (% by weight of trioxane based on the total liquid composition at said feeding plate) in the range satisfying the following relationship:

$$100 - \frac{50}{(\gamma - 0.5)} - 2(\gamma - 1)^{0.2} \leq X \quad (1)$$

$$\leq 100 - \frac{50}{(\gamma - 0.5)} - 2(\gamma - 1)^{0.2} + 2R^{0.5}$$

wherein R is reflux ratio, and $\gamma$ is a parameter defined by the following equation:

$$\gamma = \frac{R(1 - C/100) + q}{R(1 - C/100) - C/100 + q} \quad (2)$$

wherein q is the proportion of the liquid part in the fed starting material expressed in terms of ratio by weight and C (%) is the concentration of trioxane in the fed starting material.

In the hitherto known process for distilling and separating a benzene solution of trioxane, it is conventional to operate the distillation column so that the liquid composition at the starting material feeding plate coincides with the intersecting point of the operation line of concentrating part and the starting material line (q line) (for example, cf. pages 40–47 of Shigebumi Fujita and Heiichiro Tohata: Chemical Enginnering III, Ed. 2, Material Transfer Operation, published by Tokyo Kagaku Dojin). That is, when the starting material is in the state of a liquid having a temperature equal to the boiling point, it has been considered that the fundamental procedure is to approximately equalize the trioxane concentration in the liquid at the starting material feeding plate to the concentration of starting material. By such an operation, however, the removal of chain transfer agent is insufficient so that a procedure for removing the chain transfer agent by an additional rectification is needed. Contrariwise, according to the process of this invention there can be obtained a trioxane of high purity directly without any procedure of rectification. That is, it is important in this invention to maintain the trioxane concentration in the liquid at the starting material feeding plate in the range specified in this invention in order to decrease the contents of water and formic acid, which are chain transfer agents, in trioxane.

According to this invention, the trioxane concentration in the liquid at the starting material feeding plate is maintained at a markedly lower level than in the hitherto known fractional distillation process. In order to make this point clearer, the trioxane concentration in the liquid at the starting material feeding plate in the hitherto known process is compared with that in the process of this invention, in Table 1.

$$0 \leq \frac{X - \left(100 - \frac{50}{(\gamma - 0.5)} - 2(\gamma - 1)^{0.2}\right)}{2R^{0.5}} \leq 1$$

As has been mentioned above, according to this invention, a trioxane of high quality, i.e. a trioxane having a total content of chain transfer agents (water and/or formic acid) of 10 ppm or less and further 6 ppm or less, can be separated. When a polyoxymethylene having a high degree of polymerization is to be produced, the content of chain transfer agents poses a particularly important problem and it is required to purify the trioxane so that the content of formic acid comes to 4 ppm or less and more preferably 3 ppm or less. This invention

TABLE 1

| Operating conditions | | | Hitherto known process Intersecting point of operation line in the concentrating part and starting material line (q line) (%) | Process of this invention Result of calculation according to equation (1): (A) − (B)* (%) | Note γ value according to equation (2) |
|---|---|---|---|---|---|
| Concentration of starting material C (%) | State, q | Reflux ratio R | | | |
| 40 | Liquid, 1 | 3 | 40 | 23–27 | 1.17 |
| 40 | Vapor, 0 | 3 | 54 | 34–38 | 1.29 |
| 49 | Liquid, 1 | 5 | 49 | 23–27 | 1.16 |
| 32 | Liquid, 1 | 2 | 32 | 22–25 | 1.16 |
| 40 | Liquid, 1 | 1.5 | 40 | 33–36 | 1.27 |
| 40 | Liquid, 1 | 6 | 40 | 15–20 | 1.10 |
| 40 | Liquid-Vapor, 0.5 | 3 | 46 | 28–32 | 1.21 |

(*)
$A = 100 - \frac{50}{(\gamma - 0.5)} - 2(\gamma - 1)^{0.2}$ $B = 100 - \frac{50}{(\gamma - 0.5)} - 2(\gamma - 1)^{0.2} + 2R^{0.5}$ As is apparent from Table 1, a sufficiently reliable result can be obtained even by using the heading two figures of the numerical values obtained from the left and right members of equation (1). If trioxane concentration in the liquid composition at the starting material feeding plate is maintained at a value lower than the range of this invention, the separation between trioxane and benzene is difficult. On the other hand, if it is maintained at a concentration higher than the range, the contents of the chain transfer agents are difficult to decrease. The trioxane concentration in the liquid composition at the feeding plate can be controlled by increasing or decreasing the amount of ascending vapor at the column bottom, by changing the temperature profile in the column, or by other methods.

The ground for the limitation on the trioxane concentration of liquid composition at the starting material feeding plate in this invention will be explained below more concretely with reference to data.

The drawing attached illustrates that, in the distillation and separation of trioxane-containing benzene solution, the content of formic acid in the purified trioxane obtained from the column bottom is dependent upon the operating conditions of the distillation column and the trioxane concentration in the liquid composition at the starting material feeding plate. That is, it indicates that the concentration of formic acid in the product trioxane is low when the trioxane concentration in the liquid composition at the starting material feeding plate (X) satisfies the following relationship;

can meet even such a requirement.

As the trioxane-containing benzene solution used in this invention, those having a trioxane content of 10–70% by weight are preferably used and those having a trioxane content of 30–50% by weight are most preferably used, from the viewpoint of effective separation.

Although the proportions of the liquid and the gas in the starting material fed to the starting material feeding plate of distillation column are not particularly limited, it is preferable that the proportion of the liquid part is in the range of 0.5–1.0 as expressed in terms of ratio by weight.

The reflux ratio employed in the distillation and separation of trioxane and benzene varies depending on the trioxane concentration in the fed starting material liquid. However, it is usually in the range of 1.1–8. Though a reflux ratio higher than 8 is also employable, it is disadvantageous in that a uselessly high reflux ratio only brings about a loss in energy. The preferable range is 1.2–6 and the more preferable range is 1.5–4.

For the continuous distillation, a multi-plate type of rectification column is usually employed. Though distillation columns having a plate number of 30 or more are preferable, it varies depending upon the aimed accuracy of separation, the fed starting material, the reflux ratio, etc.

Hereunder, the essentiality of this invention will be explained with reference to examples, which do not limit the scope of this invention.

EXAMPLE 1

A 60% aqueous solution of formaldehyde was heated and distilled in the presence of a sulfuric acid catalyst to obtain an azeotropic mixture comprising 50% of trioxane, 10% of formaldehyde and the residual percentage of water. The azeoptropic mixture was countercurrentwise extracted with benzene to obtain a benzene solution containing 40% of trioxane. The benzene solution was continuously fed into a distillation column of 55 plates in the state of a liquid having a temperature equal to the boiling point and rectified under a condition of reflux ratio 3, while continuously separating benzene from the column top and trioxane from the column bottom. The operating conditions were controlled so as to keep the trioxane concentration in the liquid composition at the feeding plate at 26% according to the aforementioned equation (1).

The amounts of chain transfer agents in the trioxane obtained were 1 ppm of water and 1 ppm of formic acid.

A copolymerization was carried out in an ampoule at 80° C. for 5 minutes by using this trioxane, ethylene oxide (2% by weight based on the trioxane), boron trifluoride dibutyl etherate as a polymerization catalyst (0.008% by weight based on the trioxane) and methylal as a molecular weight regulator (0.1% by weight based on the trioxane). The polymerization yield of the polymer thus obtained was 90%, and its reduced viscosity was 1.8 as measured at 60° C. in a solvent mixture comprising tetrachlorethane and p-chlorophenol. A film produced by the compression molding of this polymer was tough.

COMPARATIVE EXAMPLE 1

The procedure of Example 1 was repeated, except that the operating conditions of the distillation column were selected so as to keep the trioxane concentration in the liquid composition at the feeding plate at 40% which was the same as the trioxane concentration in the starting material. The trioxane thus obtained contained 12 ppm of water and 13 ppm of formic acid.

Then, a copolymerization was carried out under the same conditions as in Example 1. As the result, the polymerization yield was 40% which was quite disadvantageous for the production of polymer. The polymer thus obtained had a reduced viscosity of 1.3, and a film produced therefrom in the same manner as above was brittle.

EXAMPLE 2

In the procedure of Example 1, the whole of starting material was fed in the state of vapor having a temperature equal to the boiling point in place of feeding it in the state of liquid. Rectification was carried out under a condition of reflux ratio 3, while continuously withdrawing benzene from the column top and trioxane from the column bottom. The operating conditions were selected so as to keep the trioxane concentration in the liquid composition at the feeding plate at 35% according to the aforementioned equation (1). The chain transfer agents present in the trioxane thus obtained were 2 ppm of water and 2 ppm of formic acid.

COMPARATIVE EXAMPLE 2

The procedure of Example 2 was repeated, except that the trioxane concentration in the liquid composition at the starting material feeding plate was 54% which was a value corresponding to the intersecting point of the operation line of concentrating part of McCabe-Thiele and the starting material line (q line) so that the operating conditions were the most preferable ones in the usual sense. The trioxane thus obtained contained 21 ppm of water and 35 ppm of formic acid.

EXAMPLE 3

In the same manner as in Example 1, the distilling trioxane was extracted with benzene to obtain a benzene solution containing 49% of trioxane. This benzene solution was fed into a distillation column of 45 plates and rectified under a condition of reflux ratio 5, while separating benzene from the column top and trioxane from the column bottom. The operating conditions were selected so as to keep the trioxane concentration in the liquid composition at the feeding plate at 24% according to the aforementioned equation (1). The chain transfer agents present in the trioxane were 0.8 ppm of water and 1 ppm of formic acid.

COMPARATIVE EXAMPLE 3

The procedure of Example 2 was repeated, except that, in Example 3, the trioxane concentration in the liquid composition at the feeding plate was kept at 49%. The chain transfer agents present in the trioxane thus obtained were 12 ppm of water and 26 ppm of formic acid.

EXAMPLE 4

In the same manner as in Example 1, the distilling trioxane was extracted with benzene to obtain a benzene solution containing 32% of trioxane. Then, this benzene solution was continuously fed into a distillation column of 50 plates in the state of a liquid having a temperature equal to the boiling point and rectified under a condition of reflux ratio 2, while separating benzene from the column top and trioxane from the column bottom. The operating conditions were selected so as to keep the trioxane concentration in the liquid composition at the feeding plate at 23% according to the aforementioned equation (1). The chain transfer agents present in the trioxane thus obtained were 1 ppm of water and 1 ppm of formic acid.

COMPARATIVE EXAMPLE 4

The procedure of Example 3 was repeated, except that, in Example 4, the trioxane concentration in the liquid composition at the feeding plate was kept at 32%. The chain transfer agents present in the trioxane thus obtained were 12 ppm of water and 32 ppm of formic acid.

EXAMPLES 5-6

In the same manner as in Example 1, a benzene solution containing 40% of trioxane was obtained. It was continuously fed into a distillation column of 50 plates and rectified, while separating benzene from the column top and trioxane from the column bottom. The operating conditions of this rectification (reflux ratio and composition at the feeding plate) and the concentrations of chain transfer agents in the trioxane are shown in Table 2.

TABLE 2

|  |  | Example | |
|---|---|---|---|
|  |  | 5 | 6 |
| Conditions | Reflux ratio | 1.5 | 6 |
|  | Trioxane concentration at | 34 | 17 |

TABLE 2-continued

|  |  | Example | |
|---|---|---|---|
|  |  | 5 | 6 |
|  | the feeding plate (%) |  |  |
| Results | Water (ppm) | 2.5 | 0.6 |
|  | Formic acid (ppm) | 3 | 0.7 |

COMPARATIVE EXAMPLES 5–7

The procedure of Example 5 was repeated, except that the trioxane concentrations in the liquid composition at the starting material feeding plates were kept as shown in Table 3 below. The results obtained are shown in Table 3.

TABLE 3

|  |  | Comparative Example | | |
|---|---|---|---|---|
|  |  | 5 | 6 | 7 |
| Conditions | Reflux ratio | 1.5 | 6 | 6 |
|  | Trioxane concentration at the feeding plate (%) | 40 | 40 | 24 |
| Results | Water (ppm) | 13 | 9 | 5 |
|  | Formic Acid (ppm) | 36 | 23 | 10 |

EXAMPLE 7

Rectification was carried out under the same condition as in Example 1 (reflux ratio 3) while continuously withdrawing benzene from the column top and trioxane from the column bottom, except that the starting material was fed in the state of a two-phase mixture of vapor and liquid having a ratio of 0.5:0.5 by weight. The operating conditions were selected so as to keep the trioxane concentration in the liquid composition at the feeding plate at 31% according to the aforementioned equation (1). The chain transfer agents present in the trioxane thus obtained were 3 ppm of water and 3 ppm of formic acid.

COMPARATIVE EXAMPLE 8

The procedure of Example 2 was repeated, except that, in Example 7, the trioxane concentration in the liquid composition at the starting material feeding plate was kept at 46% which corresponded to the intersecting point of the operation line of concentrating part of McCabe-Thiele and the starting material line (q line). The chain transfer agents present in the trioxane thus obtained were 16 ppm of water and 19 ppm of formic acid.

What is claimed is:

1. In a process for separating trioxane by a continuous distillation comprising extracting, with benzene, the trioxane-containing distillate obtainable by heating an aqueous solution of formaldehyde, feeding the trioxane-containing benzene solution into a distillation column as a starting material, distilling out the benzene from the column top and withdrawing the trioxane from the column bottom, a process for separating trioxane which comprises retaining the trioxane concentration X in the liquid composition at the starting material feeding plate of the distillation column (% by weight of trioxane based on the total liquid composition at said feeding plate) in the range satisfying the following relationship:

$$100 - \frac{50}{(\gamma - 0.5)} - 2(\gamma - 1)^{0.2} \leq X \quad (1)$$

$$\leq 100 - \frac{50}{(\gamma - 0.5)} - 2(\gamma - 1)^{0.2} + 2R^{0.5}$$

wherein R is reflux ratio, and $\gamma$ is a parameter defined by the following equation:

$$\gamma = \frac{R(1 - C/100) + q}{R(1 - C/100) - C/100 + q} \quad (2)$$

wherein q is the proportion of the liquid part in the fed starting material expressed in terms of ratio by weight, and C (%) is the concentration of trioxane in the fed starting material.

2. A process according to claim 1, wherein the concentration of trioxane in the fed starting material is 30–50%.

3. A process according to claim 1, wherein said reflux ratio is 1.2–6.

4. A process according to claim 1, wherein the proportion of liquid part in the fed starting material is 0.5–1.0 as expressed in terms of ratio by weight.

* * * * *